(12) United States Patent
Miyazaki et al.

(10) Patent No.: US 10,111,423 B2
(45) Date of Patent: Oct. 30, 2018

(54) **MICROBIAL PESTICIDE COMPOSITION OF DRIED *BACILLUS***

(71) Applicants: SDS BIOTECH K.K., Tokyo (JP); Idemitsu Kosan Co., Ltd., Tokyo (JP)

(72) Inventors: Mutsumi Miyazaki, Ibaraki (JP); Yusuke Amaki, Ibaraki (JP); Keijitsu Tanaka, Ibaraki (JP); Yasuyuki Morishita, Ibaraki (JP); Takanori Eguchi, Ibaraki (JP)

(73) Assignees: SDS BIOTECH K.K., Tokyo (JP); Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 15/302,695

(22) PCT Filed: Apr. 7, 2015

(86) PCT No.: PCT/JP2015/060816
§ 371 (c)(1),
(2) Date: Oct. 7, 2016

(87) PCT Pub. No.: WO2015/156274
PCT Pub. Date: Oct. 15, 2015

(65) Prior Publication Data
US 2017/0027166 A1    Feb. 2, 2017

(30) Foreign Application Priority Data

Apr. 9, 2014    (JP) .................................. 2014-080228

(51) Int. Cl.
*A01N 63/02*    (2006.01)
*A01N 25/22*    (2006.01)

(52) U.S. Cl.
CPC ............. *A01N 25/22* (2013.01); *A01N 63/02* (2013.01)

(58) Field of Classification Search
None
See application file for complete search history.

(56) References Cited

U.S. PATENT DOCUMENTS

| | | | | |
|---|---|---|---|---|
| 9,504,257 | B2 * | 11/2016 | Amaki | .................. A01N 63/00 |
| 2010/0272701 | A1 * | 10/2010 | Chen | ..................... A01N 63/02 |
| | | | | 424/93.462 |
| 2012/0135017 | A1 | 5/2012 | Harel et al. | |
| 2012/0149108 | A1 * | 6/2012 | Tanabe | ................. A01N 1/0221 |
| | | | | 435/374 |
| 2014/0179528 | A1 | 6/2014 | Amaki et al. | |
| 2017/0027177 | A1 * | 2/2017 | Amaki | ................... A01N 63/00 |

FOREIGN PATENT DOCUMENTS

| | | |
|---|---|---|
| CA | 1 229 806 A | 12/1987 |
| CN | 102919272 A | 2/2013 |
| CN | 104247717 A | 12/2014 |
| JP | 60-180588 A | 9/1985 |
| JP | 8-175919 A | 7/1996 |
| JP | 2000-264807 A | 9/2000 |
| JP | 2000-264808 A | 9/2000 |
| JP | 2004-35421 A | 2/2004 |
| JP | 2005-325077 A | 11/2005 |
| JP | 2009-196920 A | 9/2009 |
| JP | 2010-143856 A | 7/2010 |
| JP | 2011-184370 A | 9/2011 |
| JP | 2012-527898 A | 11/2012 |
| WO | 2012/161160 A1 | 11/2012 |

OTHER PUBLICATIONS

V. Yanez-Mendizabal et al., "Formulation development of the biocontrol agent *Bacillus subtilis* strain CPA-8 by spray-drying", Journal of Applied Microbiology, 2012, pp. 954-965, vol. 112.
International Search Report for PCT/JP2015/060816 dated Jul. 7, 2015.

* cited by examiner

*Primary Examiner* — Ralph J Gitomer
(74) *Attorney, Agent, or Firm* — Sughrue Mion, PLLC

(57) ABSTRACT

The present invention relates to a microbial pesticide composition, which is obtained by a method including the steps of: adjusting a pH of a culture solution of the *Bacillus* sp. bacterium to from 3.0 to 5.0 (pH adjustment step); mixing the culture solution with the calcium chloride and/or the magnesium sulfate (mixing step); and lyophilizing or spray-drying the culture solution (drying step). In the microbial pesticide composition, even if it is stored for a long period of time at room temperature, the active ingredient remains stable and a sufficient preventive effect against plant disease can be maintained.

12 Claims, 1 Drawing Sheet

[Fig. 1]
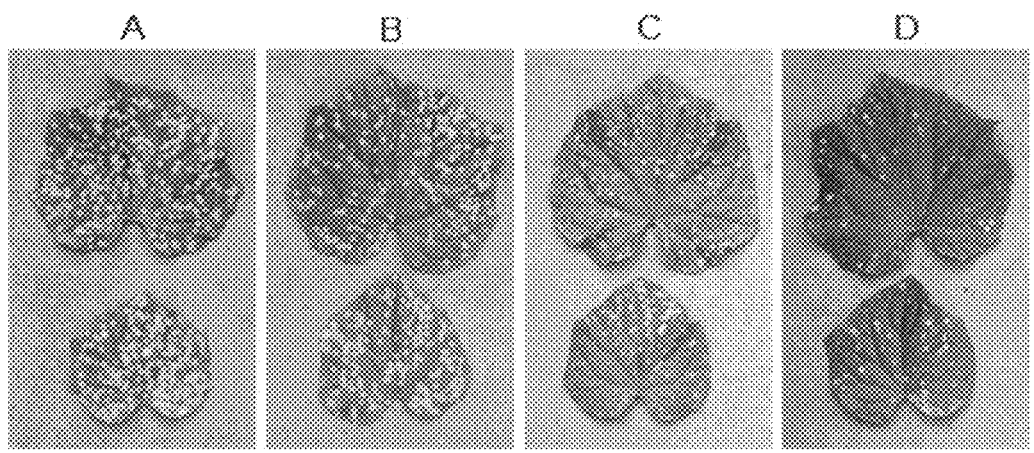
[Fig. 2]
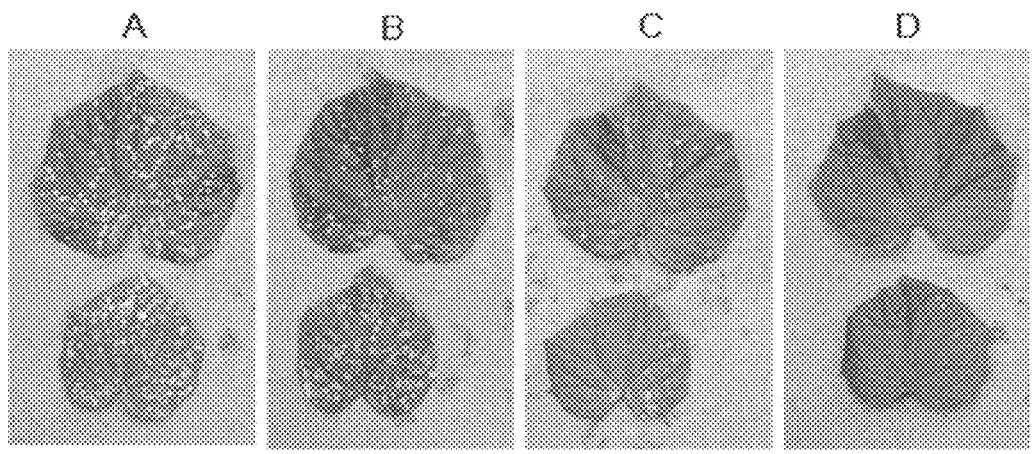

MICROBIAL PESTICIDE COMPOSITION OF DRIED *BACILLUS*

CROSS REFERENCE TO RELATED APPLICATIONS

This application is a National Stage of International Application No. PCT/JP2015/060816 filed Apr. 7, 2015.

TECHNICAL FIELD

The present invention relates to stabilization of a microbial pesticide. More specifically, the present invention relates to a microbial pesticide composition capable of keeping a plant disease-preventive effect of a *Bacillus* sp. bacterium for a long period of time, a method of manufacturing the same, and a method of stabilizing a microbial pesticide containing a *Bacillus* sp. bacterium as an active ingredient.

BACKGROUND ART

In recent years, as a method of protecting a plant from various diseases, there has been widely used a microbial pesticide that uses a microbe antagonistic to pathogens causing various diseases in consideration of safety and sustenance of an effect. In general, the microbial pesticide has an adjuvant added into its formulation in order to prevent a reduction in the effect of an active ingredient in its composition and to improve storage stability. For example, with regard to a *Bacillus* sp. bacterium that forms spores, in JP 2011-184370 A (Patent Document 1), there is a proposal to add a wettable composition containing a bacterial cell dried product, calcium sulfate, and a surfactant.

In addition, in JP 2004-35421 A (Patent Document 2), there is a proposal of a microbial pesticide containing a microbe, a clay mineral, a surfactant, and a drying agent. As the drying agent, there are specifically disclosed silica gel, calcium chloride, and calcium sulfate anhydrite III.

Meanwhile, in order to improve long-term storage stability of a bacterial cell dried product also in a microbial pesticide formulation that uses a microbe that does not form spores, investigations have been made on adjuvants. For example, JP 2005-325077 A (Patent Document 3) discloses a method involving mixing a *Pseudomonas* sp. bacterium with trehalose and then lyophilizing the mixture, to thereby obtain a microbe dried product that is satisfactory in terms of recovery rate of viable bacteria and storability as well. As a method further improved on the above-mentioned method, JP 2009-196920 A (Patent Document 4) discloses a method involving mixing a *Pseudomonas* sp. bacterium with trehalose or sucrose, and with sodium chloride and potassium chloride, and then lyophilizing the mixture, to thereby improve storage stability in a package.

In addition, each of JP 2000-264807 A (Patent Document 5) and JP 2000-264808 A (Patent Document 6) teaches that an *Erwinia* sp. bacterium or a *Pseudomonas* sp. bacterium is stored in a stable state by adding zeolite, molecular sieves, silica gel or the like as an adsorbent having an ammonia-adsorbing ability.

Further, as an example of a microbial pesticide formulation containing filamentous fungus spores as an active ingredient and having improved storage stability, JP 2010-143856 A (Patent Document 7) discloses a method involving incorporating amorphous silica into a viable fungal body of a *Fusarium* sp. fungus, and further adding calcium carbonate and/or magnesium sulfate, to thereby improve storage stability.

However, in each of the inventions of those patent documents, the stability of the microbial pesticide formulation cannot be said to have been sufficiently improved, and there has been a problem in that a plant disease-preventive effect of the microbial pesticide formulation as manufactured cannot be maintained for a long period of time.

PRIOR ART

Patent Documents

[Patent Document 1] JP 2011-184370 A
[Patent Document 2] JP 2004-35421 A
[Patent Document 3] JP 2005-325077 A
[Patent Document 4] JP 2009-196920 A
[Patent Document 5] JP 2000-264807 A
[Patent Document 6] JP 2000-264808 A
[Patent Document 7] JP 2010-143856 A

SUMMARY OF INVENTION

Problem to be Solved by Invention

An object of the present invention is to provide a microbial pesticide composition in which an active ingredient is stable even during long-term storage at room temperature, to thereby sustain a sufficient plant disease-preventive effect.

Means to Solve Problem

The inventors of the present invention have made extensive investigations in order to achieve the above-mentioned object, and as a result, have found that a bacterial cell dried product obtained by adding and mixing calcium chloride and/or magnesium sulfate into a culture solution of a *Bacillus* sp. bacterium serving as a microbe for preventing plant disease, and lyophilizing or spray-drying the culture solution is excellent in storage stability, and keeps a sufficient plant disease-preventive effect for a long period of time. Thus, the present invention has been completed.

That is, the present invention relates to microbial pesticide compositions according to the following items (1) to (9), methods of manufacturing a microbial pesticide composition according to the following items (10) and (11), and methods of stabilizing a microbial pesticide composition according to the following items (12) and (13).

(1) A microbial pesticide composition, comprising: a bacterial cell dried product of a *Bacillus* sp. bacterium; and calcium chloride and/or magnesium sulfate.

(2) The microbial pesticide composition according to (1) above, comprising a bacterial cell dried product of the *Bacillus* sp. bacterium and calcium chloride.

(3) The microbial pesticide composition according to (1) above, comprising a bacterial cell dried product of the *Bacillus* sp. bacterium and magnesium sulfate.

(4) The microbial pesticide composition according to any one of (1) to (3) above, in which a content of calcium chloride and/or magnesium sulfate is from 1 mass % to 5 mass %.

(5) The microbial pesticide composition according to any one of (1) to (4) above, in which the *Bacillus* sp. bacterium is *Bacillus subtilis* or *Bacillus amyloliquefaciens*, or a mutant strain thereof.

(6) The microbial pesticide composition according to any one of (1) to (5) above, in which the *Bacillus* sp. bacterium is a *Bacillus amyloliquefaciens* AT-332 strain, or a mutant strain thereof.

(7) The microbial pesticide composition according to any one of (1) to (6) above, which is obtained by a method comprising the steps of: adjusting a pH of a culture solution of the *Bacillus* sp. bacterium to from 3.0 to 5.0 (pH adjustment step); mixing the culture solution with the calcium chloride and/or the magnesium sulfate (mixing step); and lyophilizing or spray-drying the culture solution (drying step).

(8) The microbial pesticide composition according to (7) above, which is obtained by a method including performing the drying step after: performing the mixing step after the pH adjustment step; simultaneously performing the pH adjustment step and the mixing step; or performing the pH adjustment step after the mixing step.

(9) The microbial pesticide composition according to any one of (1) to (8) above, in which a suspended aqueous solution obtained by suspending the pesticide composition in distilled water has a pH of from 3.0 to 5.0.

(10) A method of manufacturing a microbial pesticide composition, comprising the steps of: adjusting a pH of a culture solution of a *Bacillus* sp. bacterium to from 3.0 to 5.0 (pH adjustment step); mixing the culture solution with calcium chloride and/or magnesium sulfate (mixing step); and lyophilizing or spray-drying the culture solution (drying step).

(11) The method of manufacturing a microbial pesticide composition according to (10) above, in which the drying step is performed after: performing the mixing step after the pH adjustment step; simultaneously performing the pH adjustment step and the mixing step; or performing the pH adjustment step after the mixing step.

(12) A method of stabilizing a microbial pesticide, comprising the steps of: adjusting a pH of a culture solution of a *Bacillus* sp. bacterium to from 3.0 to 5.0 (pH adjustment step); mixing the culture solution with calcium chloride and/or magnesium sulfate (mixing step); and lyophilizing or spray-drying the culture solution (drying step).

(13) The method of stabilizing a microbial pesticide according to (12) above, in which the drying step is performed after: performing the mixing step after the pH adjustment step; simultaneously performing the pH adjustment step and the mixing step; or performing the pH adjustment step after the mixing step.

Effects of Invention

According to the present invention, the active ingredient (bacterial cell dried product of the *Bacillus* sp. bacterium) in the microbial pesticide composition can be stably kept, and hence a state of having a sufficient plant disease-preventive effect can be maintained for a long period of time.

BRIEF DESCRIPTION OF DRAWINGS

FIG. 1A to FIG. 1D are photographs for showing the results of a preventive effect test (Example 2) of a microbial pesticide composition (formulation) of the present invention against cucumber powdery mildew. FIG. 1A: control plot 1 (no formulation administration), FIG. 1B: control plot 2 (no-calcium chloride-added formulation plot), FIG. 1C: 5%-calcium chloride-added/pH-non-adjusted plot, FIG. 1D: 5%-calcium chloride-added/pH 4.0 plot.

FIG. 2A to FIG. 2D are photographs for showing the results of a preventive effect test (Example 3) of the microbial pesticide composition (formulation) of the present invention against cucumber powdery mildew. FIG. 2A: control plot (no-calcium chloride-added plot), FIG. 2B: 1%-calcium chloride-added plot, FIG. 2C: 2.5%-calcium chloride-added plot, FIG. 2D: 5%-calcium chloride-added plot.

MODE FOR CARRYING OUT INVENTION

A microbial pesticide composition of the present invention contains a bacterial cell dried product of a *Bacillus* sp. bacterium serving as an active ingredient, and further contains calcium chloride and/or magnesium sulfate. Details are described below.

[*Bacillus* sp. Bacterium]

The *Bacillus* sp. bacterium to be used as the bacterial cell dried product in the microbial pesticide composition of the present invention is not particularly limited, but is preferably a *Bacillus* sp. bacterium having a preventive ability against plant disease. For example, there are given *Bacillus subtilis*, *Bacillus amyloliquefaciens*, *Bacillus pumilus*, *Bacillus cereus*, *Bacillus licheniformis*, *Bacillus velezensis*, *Bacillus* sp., and mutant strains thereof. Of those, *Bacillus subtilis*, *Bacillus amyloliquefaciens*, and mutant strains thereof, which have high preventive abilities against plant disease, are preferred, and there are more preferably given a *Bacillus amyloliquefaciens* AT-332 strain and a mutant strain thereof.

The *Bacillus amyloliquefaciens* AT-332 strain was internationally deposited at NITE Patent Microorganisms Depositary (2-5-8 Kazusakamatari, Kisarazu-shi, Chiba 292-0818, Japan) on May 2, 2011 with an accession number of NITE BP-1095.

The *Bacillus* sp. bacterium that may be used in the present invention is not limited to the above-mentioned examples, and may be any other *Bacillus* sp. bacterium. In addition, one kind or two or more kinds of bacteria may be used in combination without any problem.

[Microbial Pesticide Formulation]

The microbial pesticide composition to be used in the present invention contains a bacterial cell dried product obtained by drying a microbial culture solution by any one of the following methods: lyophilizing and spray-drying.

The drying of the microbial culture solution may be performed after the addition of calcium chloride and/or magnesium sulfate and the adjustment of its pH to from 3.0 to 5.0 have been performed.

The microbial pesticide composition of the present invention includes a bacterial cell dried product prepared by a method including the steps of: adjusting the pH of the microbial culture solution to from 3.0 to 5.0 (pH adjustment step); mixing the microbial culture solution with calcium chloride and/or magnesium sulfate (mixing step); and lyophilizing or spray-drying the microbial culture solution (drying step). Specifically, the bacterial cell dried product may be obtained by: (1) mixing the microbial culture solution with calcium chloride and/or magnesium sulfate, and then adjusting its pH to from 3.0 to 5.0, followed by drying; (2) adjusting the pH of the microbial culture solution to from 3.0 to 5.0, and then mixing the microbial culture solution with calcium chloride and/or magnesium sulfate, followed by drying; or (3) mixing the microbial culture solution with calcium chloride and/or magnesium sulfate while adjusting the pH of the microbial culture solution to from 3.0 to 5.0, followed by drying.

It is preferred that the calcium chloride and/or the magnesium sulfate be added at a concentration of from 1 mass % to 5 mass % with respect to the microbial pesticide composition (hereinafter sometimes referred to as "microbial pesticide formulation"), more preferably at a concentration of from 2.5 mass % to 5 mass % with respect to the microbial pesticide formulation. When the addition amount of the calcium chloride and/or the magnesium sulfate is less than 1 mass % with respect to the microbial pesticide formulation, a sufficient storage stability-improving effect is not obtained owing to the insufficient addition amount. In addition, a microbial pesticide formulation having calcium chloride and/or magnesium sulfate added in an amount of more than 5 mass % with respect to the formulation is unsuitable because the formulation is liable to solidify owing to the hygroscopicity of the calcium chloride and/or the magnesium sulfate, to thereby fail to provide the original effect of the microbial pesticide formulation.

The calcium chloride and the magnesium sulfate may each be used alone, or may be used in combination of both.

The microbial pesticide formulation of the present invention may contain any other optional ingredient depending on a desired dosage form and effect.

Examples of the dosage form include a granule, a powder, a granular wettable powder, a wettable powder, a water-soluble powder, a suspended formulation, and an emulsion. Of those, a granular wettable powder, a wettable powder, a water-soluble powder, or a granule is preferred, and a wettable powder is more preferred.

The optional ingredient is not particularly limited as long as the optional ingredient does not impair the effect of the present invention. Examples thereof include a carrier, a surfactant, a dispersant, an adjuvant, and a protective agent. When such optional ingredient does not affect the adjustment of the pH of the culture solution of the *Bacillus* sp. bacterium, the optional ingredient may be added together with the calcium chloride and/or the magnesium sulfate before the lyophilization during the manufacture of the microbial pesticide composition. In general, however, the optional ingredient is added and mixed into the bacterial cell dried product, and then the mixture is processed into a desired dosage form.

Examples of the carrier include: porous solid carriers such as talc, bentonite, kaolin, clay, diatomaceous earth, white carbon, vermiculite, slaked lime, ammonium sulfate, silica sand, and urea; and liquid carriers such as water, isopropyl alcohol, methylnaphthalene, xylene, cyclohexanone, and an alkylene glycol.

Examples of the surfactant and the dispersant include a dinaphthylmethanesulfonate, an alcohol sulfate, a lignosulfonate, an alkyl aryl sulfonate, a polyoxyethylene glycol ether, a polyoxyethylene sorbitan monoalkylate, and a polyoxyethylene alkyl aryl ether.

Examples of the adjuvant include carboxymethylcellulose, polyethylene glycol, propylene glycol, gum arabic, and xanthan gum, and examples of the protectant include skim milk and a pH buffer.

[Manufacture of Microbial Pesticide Composition]

The microbial pesticide composition of the present invention contains a microbe in the form of a bacterial cell dried product. The bacterial cell dried product of the microbe may be obtained using a known apparatus under known conditions.

For example, when the microbe is a *Bacillus amyloliquefaciens* AT-332 strain, the bacterial cell dried product is obtained as described below. The microbe is subjected to shaking culture in a liquid standard medium (polypeptone: 0.5%, glucose: 0.1%, yeast extract: 0.5%, pH 7.0). After that, the resultant is mixed with calcium chloride and/or magnesium sulfate and adjusted to a pH of from 3.0 to 5.0, and lyophilized or spray-dried.

The lyophilization or the spray-drying may be performed under the conditions of a known apparatus to provide the bacterial cell dried product as powder.

The resultant bacterial cell dried product may be mixed with an optional ingredient selected depending on a desired dosage form, to thereby produce the microbial pesticide composition (formulation).

[Use of Microbial Pesticide Composition (Formulation)]

The microbial pesticide composition of the present invention may be directly applied as it is, or may be applied after being diluted with water or the like. A suspended aqueous solution obtained by suspending the microbial pesticide composition of the present invention in distilled water preferably has a pH of from 3.0 to 5.0.

A method of applying the microbial pesticide composition is not particularly limited, and examples thereof include: a method of directly spraying the microbial pesticide composition onto a plant; a method of spraying the microbial pesticide composition onto soil; a method of directly coating seeds of a plant with the microbial pesticide composition; and a method of adding the microbial pesticide composition to water or a fertilizer to be added to a plant or soil. In addition, the amount of the formulation to be applied varies depending on, for example, a target disease, a target crop, the application method, the tendency of incidence, the degree of damage, environmental conditions, and the dosage form to be used, and hence is preferably adjusted as appropriate.

The microbial pesticide composition of the present invention exhibits excellent preventive capabilities against a variety of bacteria and filamentous fungi. Examples of the pathogens causing plant disease that can be prevented by the microbial pesticide composition of the present invention include, but are not limited thereto:

for "rice", *Pyricularia oryzae, Cochliobolus miyabeanus, Rhizoctonia solani*, and *Gibberella fujikuroi*;

for "winter cereals", *Erysiphe graminis* f.sp. *hordei, Erysiphe graminis* f.sp. *tritici, Puccinia striiformis, Puccinia graminis, Puccinia recondita* f.sp. *tritici, Puccinia hordei, Gibberella zeae, Pyrenophora teres, Typhula incarnata, Typhula ishikariensis, Sclerotinia borealis, Micronectriella nivalis, Ustilago nuda, Tilletia caries, Tilletia foetida, Tapesia yallundea, Phynchosporium secalis* f.sp. *hordei, Septoria tritici*, and *Leptosphaeria nodorum*;

for "citrus plants", *Diaporthe citri, Elsinoe fawcettii, Phytophthora citrophthora, Penicillium digitatum*, and *Penicillium italicum*;

for "apple", *Monilinia mali, Valsa ceratosperma, Podosphaera leucotricha, Alternata* alternate pathotype apple, *Venturia inaequalis, Gymnosporangium yamadae, Botryosphaeria berengeriana* f.sp. *piricola, Zygophiala jamaicensis, Gloeodes pomigena, Mycosphaerella pomi, Glomerella cingulata*, and *Diplocarpon mali*;

for "pear", *Venturia nashicola, Alternaria alternata* Japanese pear pathotype, *Physalospora piricola*, and *Gymnosporangium asiaticum*;

for "peach", *Monilinia fructicola, Cladosporium carpophilum*, and *Phomopsis* sp.;

for "grape", *Pseudocercospora vitis, Marssonina viticola, Elsinoe ampelina, Glomerella cingulata, Uncinula necator, Phakopsora ampelopsidis*, and *Phomopsis* sp.;

for "Japanese persimmon", *Phyllactinia kakicola, Colletotrichum gloeosporioides, Cercospora kaki*, and *Mycosphaerella nawae*;
for "Japanese apricot", *Cladosporium carpophilum;*
for "cherry", *Monilinia fructicola;*
for "gourds", *Sphaerotheca fuliginea, Didymella bryoniae*, and *Colletotorichum lagenarium*,
for "tomato", *Alternaria solani* and *Cladosporium fulvum;*
for "eggplant", *Phomopsis vexans* and *Erysiphe cichoracearum;*
for "*brassica* vegetables", *Alternaria japonica, Alternaria bracicae, Alternaria brassicicola*, and *Cercosporella brassicae;*
for "green onion", *Puccinia allii;*
for "ginger", *Pythium ultimum* and *Pythium zingiberis;*
for "strawberry", *Sphaerotheca humuli* and *Glomerella cingulata;*
for "soybeans", *Cercospora kikuchii, Elsinoe glycines*, and *Diaporthe phaseolorum* var. *sojae;*
for "azuki beans", *Cercospora canescens* and *Uromyces phaseoli* var. *azukicola;*
for "kidney beans", *Colletotrichum lindemuthianum;*
for "peanuts", *Cercosporidium personatum, Cercospora arachidicola*, and *Sphaceloma arachidis;*
for "peas", *Erysiphe pisi;*
for "potato", *Alternaria solani;*
for "tea", *Exobasidium reticulatum, Elsinoe leucospila, Pestalotiopsis theae*, and *Pestalotiopsis longiseta;*
for "tabacco", *Alternaria longipes, Erysiphe cichoracearum*, and *Colletotrichum gloeosporioides;*
for "sugar beet", *Cercospora beticola;*
for "lawn grass", *Curvularia geniculata* and *Ceratobasidium* spp.;
for "rose", *Diplocarpon rosae* and *Shaerotheca pannosa;*
for "*chrysanthemum*", *Septoria obesa* and *Puccinia horiana*; and
for "various crops", *Botrytis cinerea* and *Sclerotinia sclerotiorum.*

EXAMPLES

The present invention is specifically described below with reference to Examples. However, the present invention is not limited to the following Examples.

Example 1

The storage stability-improving effect of a microbial pesticide formulation manufactured by using a *Bacillus* sp. bacterium and adding any of various calcium compounds or magnesium compounds to a microbial culture solution after the completion of culturing was investigated.
[Manufacture of Microbial Pesticide Formulation]
  1. Preparation of Microbial Culture Solution
  100 ml of a liquid standard medium (polypeptone: 0.5 mass %, glucose: 0.1 mass %, yeast extract: 0.5 mass %, pH 7.0) was loaded into a 500 ml Erlenmeyer flask, and sterilized by heating. The medium was inoculated with 100 µl of a preculture of a *Bacillus* sp. bacterium (*Bacillus amyloliquefaciens* AT-332 strain), and the resultant was subjected to shaking culture at 30° C. and 150 rpm for 64 hours.
  2. Drying of Culture Solution and Formulation
  To the culture solution of the *Bacillus amyloliquefaciens* AT-332 strain, a calcium compound (calcium chloride, calcium acetate, calcium carbonate, calcium sulfate, calcium citrate, calcium hydrogen phosphate, calcium oxalate, or calcium pantothenate) or a magnesium compound (magnesium sulfate, magnesium chloride, or magnesium stearate) shown in Table 1 was added so as to have a final concentration of 5 mass % in a formulation, and the pH was adjusted with 5 N hydrochloric acid to 5.7, followed by drying using a lyophilizing machine. As a comparative example, a culture solution dried product not having added thereto a calcium compound or a magnesium compound was prepared. 75.1 mass % of the dried product of the culture solution was mixed with 4 mass % of trisodium citrate, 2 mass % of sodium citrate, 15.9 mass % of sodium chloride, and 3 mass % of an alkyl sulfate metal salt, and the mixture was pulverized to provide a formulation formed of a microbial pesticide composition.
[Storage Stability Test]
An aluminum laminated bag was loaded with 5 g of the formulation prepared in the foregoing, and was hermetically sealed by heat sealing. The resultant was left at rest at 54° C., and at a lapse of 3 weeks from the start of the rest, the formulation was removed from the aluminum laminated bag. The preventive effects of various formulations against various diseases were compared. As a comparative example, a formulation stored at 4° C. for 3 weeks was prepared.
[Biological Effect Test Against Cucumber Powdery Mildew]
Each formulation was adjusted through dilution with tap water by a predetermined factor to prepare a liquid agent. The diluted solution after preparation was sprayed with a hand sprayer at a rate of 40 ml per 3 pots of cucumber, and after air drying, the resultant was managed in a greenhouse. The next day, conidiospores of *Sphaerotheca cucurbitae* subcultured on cucumber leaves were suspended in a 10,000-fold diluted solution of Tween (TWEEN; trademark) 20, and adjusted with the same solution to $5\times10^3$ cells/ml. The spore suspension liquid was inoculated at about 8 ml per pot by spraying with a hand sprayer. After the inoculation, the resultant was subjected to air drying indoors, and managed in a greenhouse until investigation. After 10 to 14 days from the inoculation, a diseased area ratio was investigated, and an average diseased ratio was calculated. The diseased area ratio was judged by visual observation. In addition, a preventive value was calculated by the following equation (Math. 1), and a residual activity shown in Table 1 was calculated by the following equation (Math. 2). The residual activity is a ratio when a preventive value in the case where a microbial pesticide formulation prepared without the addition of a calcium compound or a magnesium compound into the formulation is treated at 4° C. for 3 weeks is defined as 100. The results of the biological effect test are shown in Table 1.

Preventive value (inhibition ratio) (%)=[(diseased area ratio of non-treated plot (%))−(diseased area ratio of treated plot (%))]/(diseased area ratio of non-treated plot (%))×100   [Math. 1]

Residual activity (%)=100×preventive value with addition of calcium compound or magnesium compound (%)/preventive value of control plot (%)   [Math. 2]

TABLE 1

| Adjuvant added | Storage conditions | Residual activity (%) |
|---|---|---|
| No addition | 4° C., 3 weeks | 100 |
| No addition | 54° C., 3 weeks | 12 |
| Calcium chloride | | 65 |
| Calcium acetate | | 12 |

TABLE 1-continued

| Adjuvant added | Storage conditions | Residual activity (%) |
|---|---|---|
| Calcium carbonate | | 32 |
| Calcium sulfate | | 44 |
| Calcium citrate | | 35 |
| Calcium hydrogen phosphate | | 12 |
| Calcium oxalate | | 49 |
| Calcium pantothenate | | 45 |
| Magnesium sulfate | | 61 |
| Magnesium chloride | | 44 |
| Magnesium stearate | | 47 |

As apparent from Table 1, when the formulation not having added thereto a calcium compound or a magnesium compound was subjected to the storage stability test at 54° C. for 3 weeks, the residual activity calculated on the basis of the preventive value against cucumber powdery mildew reduced to 12%. In view of this, preventive effects against cucumber powdery mildew were compared using the formulations each having a calcium compound or a magnesium compound shown in Table 1 added so as to have a final concentration of 5 mass % and subjected to the storage stability test at 54° C. for 3 weeks. The microbial pesticide formulation having added thereto, as a substance exhibiting an effect on the storage stability of a microbial pesticide formulation, calcium sulfate disclosed in Patent Document 1, calcium chloride used as a drying agent in Patent Document 2, or calcium carbonate or magnesium sulfate disclosed in Patent Document 7 exhibited a residual activity of from 30% to 65% after the heat treatment at 54° C. for 3 weeks, as shown in Table 1, thus exhibiting a storage stability-improving effect as compared to the residual activity of the comparative example, i.e., 12%. Of those, calcium chloride or magnesium sulfate, which exhibited a residual activity of 60% or more, allowed the original effect of the microbial pesticide formulation to be kept even after the heat treatment at 54° C. for 3 weeks through its addition into the formulation, and was shown to provide a storage stability-improving effect and a preventive effect against disease.

In view of the foregoing, for the purpose of further improvement in storage stability, conditions were searched for under which a residual activity in the biological effect test of 90% or more was exhibited even after the heat treatment at 54° C. for 3 weeks in the case of adding any of the two kinds of compounds that exhibited high effects in Example 1, i.e., calcium chloride and magnesium sulfate into a formulation.

Example 2

An investigation was made as to what storage stability-improving effect was obtained by adding any of the two kinds of compounds, i.e., calcium chloride and magnesium sulfate into a microbial pesticide formulation, and adjusting its pH.

Calcium chloride or magnesium sulfate was added to the culture solution of the *Bacillus amyloliquefaciens* AT-332 strain so as to have a concentration of 5% in a formulation, and the pH of the culture solution was adjusted with 5 N hydrochloric acid or 5 N sodium hydroxide to 3.0, 3.5, 4.0, 4.5, 5.0, 5.5, 6.0, or 9.0, followed by lyophilization. A formulation prepared by performing the other operations in the same manner as in Example 1 was evaluated against cucumber powdery mildew. The results are shown in Table 2.

TABLE 2

| Adjuvant added | Storage conditions | Residual activity (%) | 500-fold diluted preventive value |
|---|---|---|---|
| No adjuvant addition/no pH adjustment | 4° C., 3 weeks | 100 | 92 |
| No adjuvant addition/no pH adjustment | 54° C., 3 weeks | 5 | 5 |
| 5% Calcium chloride (no pH adjustment) | | 59 | 55 |
| 5% Calcium chloride (pH 3.0) | | 75 | 70 |
| 5% Calcium chloride (pH 3.5) | | 92 | 86 |
| 5% Calcium chloride (pH 4.0) | | 97 | 90 |
| 5% Calcium chloride (pH 4.5) | | 92 | 86 |
| 5% Calcium chloride (pH 5.0) | | 87 | 81 |
| 5% Calcium chloride (pH 5.5) | | 59 | 55 |
| 5% Calcium chloride (pH 6.0) | | 49 | 46 |
| 5% Calcium chloride (pH 9.0) | | 41 | 38 |
| 5% Magnesium sulfate (no pH adjustment) | | 57 | 53 |
| 5% Magnesium sulfate (pH 3.0) | | 71 | 66 |
| 5% Magnesium sulfate (pH 3.5) | | 76 | 71 |
| 5% Magnesium sulfate (pH 4.0) | | 82 | 76 |
| 5% Magnesium sulfate (pH 4.5) | | 78 | 73 |
| 5% Magnesium sulfate (pH 5.0) | | 74 | 69 |
| 5% Magnesium sulfate (pH 5.5) | | 52 | 48 |
| 5% Magnesium sulfate (pH 6.0) | | 34 | 32 |
| 5% Magnesium sulfate (pH 9.0) | | 20 | 19 |

As apparent from Table 2, when the formulations having added thereto calcium chloride and magnesium sulfate, respectively, serving as the related art were subjected to the storage stability test at 54° C. for 3 weeks, the formulations exhibited residual activities of 59% and 57%, respectively. Meanwhile, when the microbial pesticide formulation obtained by adding any of those salts into the culture solution after the completion of culturing, and adjusting the culture solution to a low pH was subjected to the storage stability test at 54° C. for 3 weeks, the formulation exhibited a maximum residual activity of 97% in the case of calcium chloride and a pH of 4.0, and the activity against cucumber powdery mildew was shown to increase up to about 1.6-fold as compared to the formulation only having added thereto a salt. The storage stability-improving effect based on pH adjustment was found to be remarkable in the formulation having its pH adjusted to 5.0 or less. The improving effect in the case of adjusting the pH to less than 3.0 was not investigated, but such case is considered to be unsuitable because of a safety problem such as irritation when usability as a microbial pesticide is taken into consideration. As can be seen, the microbial pesticide formulation formulated by adding calcium chloride or magnesium sulfate to the culture solution after the completion of culturing so as to have a final concentration of 5% in the formulation, and adjusting its pH to from 3.0 to 5.0, followed by drying of the culture solution, kept a high storage stability effect even after the heat treatment at 54° C. for 3 weeks, and exhibited high activity against cucumber powdery mildew. Calcium chloride was more preferred, and in particular, an excellent effect was exhibited in the case of calcium chloride and the pH range of from 3.5 to 4.5.

Among the results of Example 2, photographs in FIG. 1 are for showing the test results of comparing preventive effects against cucumber powdery mildew after formulations each having calcium chloride added into the formulation and having its pH adjusted to 4.0 have been subjected to the storage stability test at 54° C. for 3 weeks. In FIG. 1A, the results of the non-treated plot are shown. In FIG. 1B, the results of the test plot in which the formulation not having added thereto calcium chloride and not having its pH adjusted was subjected to the storage stability test at 54° C. for 3 weeks and then evaluated are shown. In FIG. 1C, the results of the test plot in which the formulation having calcium chloride added into the formulation so as to have a final concentration of 5% and not having its pH adjusted was subjected to the storage stability test at 54° C. for 3 weeks are shown. In FIG. 1D, the results of the test plot in which the formulation having calcium chloride added into the formulation so as to have a final concentration of 5% and having its pH adjusted to 4.0 was subjected to the storage stability test at 54° C. for 3 weeks and then evaluated are shown. In FIG. 1B, specks comparable to those of the non-treated plot were observed, whereas in the test plot of FIG. 1C using a formulation having added thereto calcium chloride and the test plot of FIG. 1D using a formulation having added thereto calcium chloride and having the pH adjusted to 4.0, the numbers of specks were small, and the preventive effects against cucumber powdery mildew were shown to be improved. This revealed that the preventive effect was improved by adding calcium chloride and adjusting the pH to 4.0.

Example 3

Investigation was made on the concentration of calcium chloride at which a storage stability effect and a plant disease-preventive effect were sufficiently obtained.

Calcium chloride or magnesium sulfate was added to the culture solution of the *Bacillus amyloliquefaciens* AT-332 strain so as to have a final concentration (mass %) in a formulation of 0.5%, 1.0%, 2.5%, or 5%, and the pH of the culture solution was adjusted with 5 N hydrochloric acid to 4.0, followed by lyophilization. A formulation prepared by performing the other operations in the same manner as in Example 1 was evaluated against cucumber powdery mildew. The results are shown in Table 3.

TABLE 3

| Adjuvant added | Storage conditions | Residual activity (%) |
| --- | --- | --- |
| No adjuvant addition/no pH adjustment | 4° C., 3 weeks | 100 |
| No adjuvant addition/no pH adjustment | 54° C., 3 weeks | 0 |
| 5% Calcium chloride (no pH adjustment) | | 55 |
| 0% Calcium chloride (pH 4.0) | | 42 |
| 0.5% Calcium chloride (pH 4.0) | | 42 |
| 1% Calcium chloride (pH 4.0) | | 57 |
| 2.5% Calcium chloride (pH 4.0) | | 70 |
| 5% Calcium chloride (pH 4.0) | | 88 |
| 5% Magnesium sulfate (no pH adjustment) | | 47 |
| 0% Magnesium sulfate (pH 4.0) | | 42 |
| 0.5% Magnesium sulfate (pH 4.0) | | 40 |
| 1% Magnesium sulfate (pH 4.0) | | 50 |
| 2.5% Magnesium sulfate (pH 4.0) | | 65 |
| 5% Magnesium sulfate (pH 4.0) | | 77 |

As a result, it was shown that when the concentration of calcium chloride or magnesium sulfate added into the formulation was 0.5 mass % or less as a final concentration, a residual activity of 50% or more was not obtained. This revealed that the amount of calcium chloride or magnesium sulfate in a formulation required to exhibit a storage stability-improving effect was desirably 1.0 mass % or more. In addition, although not shown in Table 3, the case where calcium chloride or magnesium sulfate is added at a final concentration of more than 5% in a formulation is unsuitable because the formulation solidifies during the storage stability test. This revealed that in order to obtain a stable storage stability effect, it was desirable to add calcium chloride or magnesium sulfate into the formulation so as to have a final concentration of from 1 mass % to 5 mass %.

Among the cases of Example 3, photographs in FIG. 2 are for comparing preventive effects against cucumber powdery mildew using formulations obtained after microbial pesticide formulations each formulated using a bacterial cell dried product obtained by adding calcium chloride to the culture solution so as to have a final concentration (mass %) of 1%, 2.5%, or 5%, and adjusting its pH with 5 N hydrochloric acid to 4.0, followed by lyophilization have been subjected to the storage stability test at 54° C. for 3 weeks. In the photograph of FIG. 2A, the results of the case of using the formulation stored at 54° C. for 3 weeks without the addition of calcium chloride into the culture solution and the adjustment of the pH are shown. In FIG. 2B, the results of the evaluation of the formulation obtained by adding calcium chloride to the culture solution so as to have a final concentration of 1%, and adjusting its pH to 4.0 are shown. In FIG. 2C, the results of the evaluation of the formulation obtained by adding calcium chloride to the culture solution so as to have a final concentration of 2.5 mass % in the formulation, and adjusting its pH to 4.0 are shown. In FIG. 2D, the results of the evaluation of the formulation obtained by adding calcium chloride to the culture solution so as to have a final concentration of 5 mass % in the formulation, and adjusting its pH to 4.0 are shown. The results reveal that in FIG. 2A, the activity is reduced to a level comparable to that of the non-treated plot, and as shown in FIG. 2B, FIG. 2C, and FIG. 2D, as the calcium chloride concentration in the formulation increases, the preventive effect against cucumber powdery mildew is improved. This revealed that in order to obtain a storage stability-improving effect by adding calcium chloride, it was desirable to add at least 1 mass % or more of calcium chloride into the formulation.

Example 4

For a disease other than cucumber powdery mildew, an investigation was made as to whether or not a similar storage stability-improving effect was obtained.

The same method as that of Example 1 was used except that the formulation subjected to the storage stability test was evaluated for its biological effect on cucumber gray mold. The details of the biological effect test with cucumber gray mold are described below.

A formulation was adjusted through dilution with tap water by a predetermined factor. 50 µl of the diluted solution was dropped on paper discs for antibiotic assay, and the paper discs were left at rest on the surfaces of cucumber cotyledons with the surfaces of the paper discs impregnated with the solution facing downward. Next, conidiospores were collected from *Botrytis cinerea* grown on a PDA agar medium, and adjusted with distilled water to $4 \times 10^5$/ml. To the spore suspension liquid, an equal amount of a nutrition solution (2% sucrose, 0.4% yeast extract) was added, and finally adjusted to $2 \times 10^5$/ml. 50 µl of the spore suspension liquid was dropped on the paper discs arranged on the cucumber cotyledons, and kept at a temperature of 21° C. for 3 days. After that, the diameter of each speck was measured. Through comparison to the speck diameter of a non-treated plot, the preventive value of each agent was calculated by the following equation (Math. 3). A residual activity ratio was calculated by the following equation (Math. 4) as a ratio when the preventive value of a formulation treated at 4° C.

for 3 weeks without the addition of any adjuvant into the formulation was defined as 100. The results are shown in Table 4.

Preventive value (%)=[(speckφ of non-treated plot)−(speckφ of treated plot)]/(speckφ of non-treated plot)×100  [Math. 3]

Residual activity (%)=100×preventive value with addition of calcium compound or magnesium compound (%)/preventive value of control plot (%)

TABLE 4

| Adjuvant added | Storage conditions | Residual activity (%) |
|---|---|---|
| No adjuvant addition/no pH adjustment | 40° C., 3 weeks | 100 |
| No adjuvant addition/no pH adjustment | 54° C., 3 weeks | 0 |
| 5% Calcium chloride addition (pH 4.0) | | 100 |

As a result, when the formulation obtained by drying the culture solution having added thereto calcium chloride and having its pH adjusted to 4.0 was subjected to the storage stability test at 54° C. for 3 weeks, the resultant microbial pesticide formulation had a residual activity of 100%. This revealed that the microbial pesticide formulation obtained by the present invention, even after the heat treatment at 54° C. for 3 weeks, had not only a preventive effect against cucumber powdery mildew but also a preventive effect against cucumber gray mold, and was not limited by the kind of the disease.

Example 5

For *Bacillus* sp. bacteria other than the *Bacillus amyloliquefaciens* AT-332 strain, an investigation was made as to whether or not similar effects were obtained.

Calcium chloride was added to each of culture solutions of a *Bacillus subtilis* QST-713 strain (isolated from Impression manufactured by SDS Biotech K.K.), a *Bacillus subtilis* MBI-600 strain (isolated from BOTOKILLER manufactured by Idemitsu Kosan Co., Ltd.), a *Bacillus subtilis* HAI-0404 strain (isolated from AgroCare manufactured by Nippon Soda Co., Ltd.), and a *Bacillus amyloliquefaciens* D747 strain (isolated from Ecoshot manufactured by Kumiai Chemical Industry Co., Ltd.) so as to have a final concentration of 5% in a formulation, and the pH was adjusted with 5 N hydrochloric acid to 4.0, followed by lyophilization. A formulation prepared by performing the other operations in the same manner as in Example 1 was evaluated against cucumber powdery mildew. The results are shown in Table 5.

TABLE 5

| Bacterial strain name | Adjuvant added | Storage conditions | Residual activity (%) |
|---|---|---|---|
| *Bacillus subtilis* QST-713 | No adjuvant addition/no pH adjustment | 4° C., 3 weeks | 100 |
| | No adjuvant addition/no pH adjustment | 54° C., 3 weeks | 16 |
| | 5% Calcium chloride addition (pH 4.0) | | 90 |
| *Bacillus subtilis* MBI-600 | No adjuvant addition/no pH adjustment | 4° C., 3 weeks | 100 |
| | No adjuvant addition/no pH adjustment | 54° C., 3 weeks | 22 |

TABLE 5-continued

| Bacterial strain name | Adjuvant added | Storage conditions | Residual activity (%) |
|---|---|---|---|
| | 5% Calcium chloride addition (pH 4.0) | 3 weeks | 94 |
| *Bacillus subtilis* HAI-0404 | No adjuvant addition/no pH adjustment | 4° C., 3 weeks | 100 |
| | No adjuvant addition/no pH adjustment | 54° C., 3 weeks | 14 |
| | 5% Calcium chloride addition (pH 4.0) | | 89 |
| *Bacillus amyloliquefaciens* D747 | No adjuvant addition/no pH adjustment | 4° C., 3 weeks | 100 |
| | No adjuvant addition/no pH adjustment | 54° C., 3 weeks | 26 |
| | 5% Calcium chloride addition (pH 4.0) | | 85 |

As a result, storage stability-improving effects similar to that of the *Bacillus amyloliquefaciens* AT-332 strain were found also in the test using the *Bacillus subtilis* QST-713 strain, the *Bacillus subtilis* MBI-600 strain, the *Bacillus subtilis* HAI-0404 strain, and the *Bacillus amyloliquefaciens* D747 strain. This revealed that a microbial pesticide formulation obtained from a *Bacillus* sp. bacterium having added thereto calcium chloride or magnesium sulfate and having the pH adjusted to from 4.0 to 5.0 exhibited a high

The invention claimed is:

1. A microbial pesticide composition, comprising: a bacterial cell dried product of a *Bacillus* sp. bacterium; and calcium chloride and/or magnesium sulfate, wherein the content of calcium chloride and/or magnesium sulfate in said composition is from 1 mass % to 5 mass %.

2. The microbial pesticide composition according to claim 1, comprising a bacterial cell dried product of the *Bacillus* sp. bacterium and calcium chloride.

3. The microbial pesticide composition according to claim 1, comprising a bacterial cell dried product of the *Bacillus* sp. bacterium and magnesium sulfate.

4. The microbial pesticide composition according to claim 1, in which the *Bacillus* sp. bacterium is *Bacillus subtilis* or *Bacillus amyloliquefaciens*, or a mutant strain thereof.

5. The microbial pesticide composition according to claim 1, in which the *Bacillus* sp. bacterium is a *Bacillus amyloliquefaciens* AT-332 strain, or a mutant strain thereof.

6. The microbial pesticide composition according to claim 1, which is obtained by a method comprising the steps of: adjusting a pH of a culture solution of the *Bacillus* sp. bacterium to from 3.0 to 5.0 (pH adjustment step); mixing the culture solution with the calcium chloride and/or the magnesium sulfate (mixing step); and lyophilizing or spray-drying the culture solution (drying step).

7. The microbial pesticide composition according to claim 6, which is obtained by a method including performing the drying step after: performing the mixing step after the pH adjustment step; simultaneously performing the pH adjustment step and the mixing step; or performing the pH adjustment step after the mixing step.

8. The microbial pesticide composition according to claim 1, in which a suspended aqueous solution obtained by suspending the pesticide composition in distilled water has a pH of from 3.0 to 5.0.

9. A method of manufacturing a microbial pesticide composition according to claim 1, comprising the steps of: adjusting a pH of a culture solution of a *Bacillus* sp. bacterium to from 3.0 to 5.0 (pH adjustment step); mixing the culture solution with calcium chloride and/or magnesium sulfate (mixing step); and lyophilizing or spray-drying the culture solution (drying step).

10. The method of manufacturing a microbial pesticide composition according to claim 9, in which the drying step is performed after: performing the mixing step after the pH adjustment step; simultaneously performing the pH adjustment step and the mixing step; or performing the pH adjustment step after the mixing step.

11. A method of stabilizing a microbial pesticide according to claim 1, comprising the steps of: adjusting a pH of a culture solution of a *Bacillus* sp. bacterium to from 3.0 to 5.0 (pH adjustment step); mixing the culture solution with calcium chloride and/or magnesium sulfate (mixing step); and lyophilizing or spray-drying the culture solution (drying step).

12. The method of stabilizing a microbial pesticide according to claim 11, in which the drying step is performed after: performing the mixing step after the pH adjustment step; simultaneously performing the pH adjustment step and the mixing step; or performing the pH adjustment step after the mixing step.

* * * * *